(12) United States Patent
Dubief et al.

(10) Patent No.: US 7,618,617 B2
(45) Date of Patent: *Nov. 17, 2009

(54) AQUEOUS HAIR TREATMENT COMPOSITIONS, THICKENED WITH AN AMPHIPHILIC LINEAR BLOCK COPOLYMER

(75) Inventors: Claude Dubief, Le Chesnay (FR); Franck Giroud, Clichy (FR)

(73) Assignee: L'Oreal, Paris (FR)

( * ) Notice: Subject to any disclaimer, the term of this patent is extended or adjusted under 35 U.S.C. 154(b) by 862 days.

This patent is subject to a terminal disclaimer.

(21) Appl. No.: 10/448,420

(22) Filed: May 30, 2003

(65) Prior Publication Data

US 2004/0009136 A1    Jan. 15, 2004

Related U.S. Application Data

(60) Provisional application No. 60/385,608, filed on Jun. 5, 2002.

(30) Foreign Application Priority Data

May 31, 2002    (FR)    .................................. 02 06729

(51) Int. Cl.
*A61Q 5/06*    (2006.01)
(52) U.S. Cl. ............... 424/70.15; 424/70.11; 424/70.16
(58) Field of Classification Search ....................... None
See application file for complete search history.

(56) References Cited

U.S. PATENT DOCUMENTS 3,907,984 A     9/1975  Calvert et al.
5,019,377 A     5/1991  Torgerson .................... 424/70
6,410,005 B1 *  6/2002  Galleguillos et al. ...... 424/70.16
6,994,846 B2 *  2/2006  L'Alloret ................ 424/78.18
2002/0160026 A1 * 10/2002 Frechet et al. ............. 424/401

FOREIGN PATENT DOCUMENTS

| EP | 0761199       | 7/1996  |
| FR | 75/39968      | 12/1975 |
| FR | 0494022       | 12/1991 |
| FR | 93/10967      | 9/1993  |
| GB | 1 512 280     | 5/1978  |
| JP | 2001-288233 A | 10/2001 |
| JP | 2004-002432   | 1/2004  |
| WO | 01/86429      | 6/2000  |
| WO | 00/40628      | 7/2000  |
| WO | 01/16187      | 3/2001  |

OTHER PUBLICATIONS

"Application of Acrylates/Methacrylates/Beheneth-25 Methacrylate Copolymer as a Thickener in Cosmetic Formulations," XP-000888570, 494 / Research Disclosure—Apr. 1999 (2 pages).

* cited by examiner

*Primary Examiner*—Jyothsna A Venkat
(74) *Attorney, Agent, or Firm*—Steptoe & Johnson LLP

(57) ABSTRACT

The invention relates to the use of a water-soluble or water-dispersible linear block copolymer comprising at least one hydrophulic block and at least one hydrophobic block, the hydrophilic block representing at least 30% by weight of the linear block copolymer, with the exclusion of block copolymers of ethylene oxide and propylene oxide, block copolymers containing urethane units and block copolymers containing siloxane units, to thicken or gel aqueous hair treatment compositions containing at least one polymer that is beneficial for the hair, and also to aqueous hair compositions thickened or gelled with such a block copolymer.

15 Claims, No Drawings

AQUEOUS HAIR TREATMENT COMPOSITIONS, THICKENED WITH AN AMPHIPHILIC LINEAR BLOCK COPOLYMER

The present application claims priority under 35 U.S.C. § 119 to U.S. Provisional Application Ser. No. 60/385,608, filed Jun. 5, 2002, the disclosure of which is expressly incorporated by reference herein in its entirety.

The present invention relates to the use of a linear block copolymer comprising at least one hydrophilic block and at least one hydrophobic block, the hydrophilic block(s) representing at least 30% by weight of the linear block copolymer, to thicken or gel aqueous hair treatment compositions containing at least one polymer that is beneficial for the hair, and to the hair compositions thus thickened or gelled.

Many thickening or gelling polymers have been proposed for formulating aqueous compositions intended for washing, caring for and styling the hair.

Among these polymers, the ones that are most frequently used are:

(1) natural polymers such as xanthan gum and guar gum, or alternatively cellulose derivatives, starches and alginates. These compounds often adversely affect the cosmetic properties of thickened compositions. Thus, in the field of hair treatment, they often give, despite the presence of conditioners, a laden feel with relatively little silkiness, occasionally a little dry and also, occasionally, a dull appearance. Their natural origin may moreover give rise to problems of reproducibility between the various batches of raw material, which is reflected by variability in the gelling power; and (2) crosslinked acrylic synthetic polymers such as the Carbopols® sold by Goodrich and crosslinked and at least partially neutralized 2-acrylamido-2-methylpropanesulphonic acid (AMPS) polymers, for instance the product sold under the name Hostacerin® AMPS by Clariant. However, to obtain reproducible viscosities, a specific and complex protocol of dispersion in water needs to be followed for these crosslinked gelling agents.

Various gelling agents have recently been proposed for limiting these problems of dispersions, for instance the Carbopols® ETD, which are particular "easy to disperse" Carbopols, or alternatively crosslinked gelling agents dispersed in an oil or a mixture of oils, such as the polyacrylamide sold by Seppic under the name Sépigel®305.

However, a specific protocol of swelling of the polymer needs to be followed to disperse the Carbopols® ETD in water, while the gelling agents supplied as a dispersion in an oil necessarily introduce surfactants and an oily phase into the composition, the phase being particularly undesirable in the case of compositions intended to be applied to the hair.

The inventors have found, surprisingly, that a particular group of block copolymers, described in greater detail hereinbelow, make it possible not only to overcome the drawbacks of the prior-art thickening and gelling polymers described above, but also have an intrinsic beneficial effect that can reinforce the action of other polymers present in the cosmetic hair compositions.

The inventors have also observed that the block copolymers used in accordance with the present invention for thickening or gelling hair treatment compositions—by virtue of their amphiphilic nature resulting from the presence, in the molecule, of a hydrophilic portion and a hydrophobic portion—give the thickened compositions excellent homogeneity, which is stable over time and which is reflected by a more transparent and more attractive appearance of the compositions.

Consequently, one subject of the present invention is the use of a water-soluble or finely water-dispersible linear block copolymer comprising at least one hydrophilic block and at least one hydrophobic block, the hydrophilic block(s) representing at least 30% by weight of the linear block copolymer, with the exclusion of block copolymers of ethylene oxide and of propylene oxide, block copolymers containing urethane units and block copolymers containing siloxane units, to thicken or gel aqueous hair treatment compositions containing at least one polymer that is beneficial for the hair.

A subject of the invention is also hair compositions containing, in a cosmetically acceptable aqueous medium,
(a) at least one polymer that is beneficial for the hair, and
(b) at least one water-soluble or finely water-dispersible linear block copolymer comprising at least one hydrophilic block and at least one hydrophobic block, the hydrophilic block(s) representing at least 30% by weight of the linear block copolymer, with the exclusion of block copolymers of ethylene oxide and propylene oxide, block copolymers containing urethane units and block copolymers containing siloxane units, in an amount that is sufficient to thicken or gel the composition.

For the purposes of the present invention, the expression "polymer that is beneficial for the hair" means a polymer that has fixing properties, i.e. that provides hold to the hair, or conditioning properties. The term "conditioning properties" means an improvement in at least one of the following properties: ease of disentangling, softness, sheen and smooth nature of the hair.

The expression "amount that is sufficient to thicken or gel" the hair composition means an amount that can give the composition a dynamic viscosity measured at a temperature of 25° C., using a Rheomat RM 180 rheometer at a shear rate of 200 s$^{-1}$, greater than 0.1 Pa·s (1 poise) and preferably greater than 0.2 Pa·s (2 poises).

The linear block copolymers that may be used according to the present invention for thickening or gelling the aqueous hair compositions are "amphiphilic" copolymers, i.e., copolymers comprising both hydrophobic blocks and hydrophilic blocks.

According to the present invention, the term "hydrophobic blocks" means blocks comprising at least 75 mol % of water-insoluble monomers, and the term "hydrophilic blocks" means blocks comprising at least 75 mol % of water-soluble monomers.

The water-soluble monomers forming the hydrophilic blocks of the block copolymers used in the present invention may be of anionic, nonionic or cationic in nature and may be used alone or in the form of a mixture containing two or more different monomers.

Examples of anionic water-soluble monomers that may be mentioned include ethylenically unsaturated carboxylic acids, such as acrylic acid, methacrylic acid, itaconic acid, fumaric acid, crotonic acid, maleic acid, 2-acrylamido-2-methylpropanesulphonic acid, styrenesulphonic acid, vinylsulphonic acid and vinylphosphonic acid.

The nonionic water-soluble monomers include, inter alia, acrylamide, $C_{1-6}$ N-alkyl or $C_{1-3}$ N,N-dialkyl acrylamides, polyethylene glycol acrylate, polyethylene glycol methacrylate, N-vinylacetamide, N-methyl-N-vinylacetamide, N-vinylformamide, N-methyl-N-vinylformamide, N-vinyllactams comprising a cyclic group of 4 to 9 carbon atoms, vinyl alcohol (copolymerized in the form of vinyl acetate and then hydrolysed), ethylene oxide, hydroxyethyl acrylate, hydroxypropyl acrylate, hydroxyethyl methacrylate and hydroxypropyl methacrylate.

Finally, the cation water-soluble monomers include, for example, dimethyldiallylammonium chloride, methylvinylimidazolium chloride, 2-vinylpyridine, 4-vinylpyridine, 2-methyl-5-vinylpyridine, vinylamine and the monomers of formula:

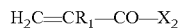

$H_2C=CR_1—CO—X_2$ in which $R_1$ represents a hydrogen atom or a methyl group; and $X_2$ represents a linear or branched $C_{1-6}$ hydrocarbon-based group bearing at least one primary, secondary or tertiary amine function or at least one quaternary nitrogen atom, or a group of formula $NHR_2$ or of formula $NR_2R_3$ in which $R_2$ and $R_3$ represent, independently of each other, a linear or branched $C_{1-6}$ hydrocarbon-based group bearing at least one primary, secondary or tertiary amine function or at least one quaternary nitrogen atom.

The water-insoluble monomers forming the hydrophobic blocks of the block copolymers are preferably chosen from vinylaromatic monomers such as styrene and its alkyl derivatives, for instance 4-butylstyrene, α-methylstyrene and vinyltoluene, dienes such as butadiene and 1,3-hexadiene, and alkyl derivatives of dienes, such as isoprene and dimethylbutadiene, chloroprene, $C_{1-10}$ alkyl, $C_{6-10}$ aryl or $C_{6-10}$ aralkyl acrylates and $C_{1-10}$ alkyl, $C_{6-10}$ aryl or $C_{6-10}$ aralkyl methacrylates, for instance methyl, ethyl, n-butyl, 2-ethylhexyl, tert-butyl, isobornyl, phenyl or benzyl (meth)acrylate, vinyl acetate, the vinyl ethers of formula $CH_2=CH—O—R$ and the allyl ethers of formula $CH_2=CH—CH_2—O—R$ in which R represents a $C_{1-6}$ alkyl group, acrylonitrile, vinyl chloride, vinylidene chloride, caprolactone, ethylene, propylene, vinyl monomers that are fluorinated or that contain a perfluoro chain, such as fluoroalkyl acrylates or methacrylates, or alkyl α-fluoroacrylates.

As indicated above with regard to the definition of the hydrophobic and hydrophilic blocks of the block copolymers, the water-insoluble monomers and the water-soluble monomers represent at least 75 mol %, respectively, of the hydrophobic and hydrophilic blocks. In other words, each hydrophobic block may comprise up to 25 mol % of one or more water-soluble monomers. This proportion is preferably not more than 10 mol % and ideally less than or equal to 5 mol %.

Analogously, each hydrophilic block may comprise up to 25 mol %, preferably up to 10 mol % and ideally up to 5 mol %, of one or more water-insoluble monomers.

The linear block copolymers used also, obviously, include those in which the hydrophilic blocks and the hydrophobic blocks consist exclusively, respectively, of water-soluble monomers and of water-insoluble monomers. These blocks may be homopolymer blocks or copolymer blocks containing two or more than two different monomers of the same type.

The term "water-soluble monomer" means a monomer which, when introduced into water at 25° C., and at a weight concentration equal to 0.5%, and optionally neutralized, allows the production of a macroscopically homogeneous and transparent solution, i.e. a solution having a light transmittance value, at a wavelength equal to 500 nm, through a sample 1 cm thick, of at least 70%, and preferably of at least 80%.

The number-average molecular mass of each block, whether it is hydrophobic or hydrophilic, or copolymeric or homopolymeric, is preferably between 500 and 100,000 and in particular between 500 and 50,000, with a polydispersity index ($M_w/M_n$) of between 1.01 and 3.0, and preferably between 1.1 and 2.5.

The linear block copolymers used in the present invention may be:
(1) diblock copolymers of formula AB;
(2) triblock copolymers of formula ABA or BAB; and
(3) multiblock copolymers comprising at least two hydrophilic blocks and at least two hydrophobic blocks arranged alternately, each block A representing a hydrophilic block and each block B representing a hydrophobic block, the blocks A of the same polymer possibly being identical or different and the blocks B of the same polymer possibly being identical or different.

Diblock copolymers and triblock copolymers comprising a hydrophilic central block and two hydrophobic side blocks are particularly preferred.

As indicated previously, the amphiphilic block copolymers used for thickening aqueous hair treatment compositions are either water-soluble or finely water-dispersible.

The terms "water-soluble" and "finely water-dispersible" mean, in the present application, polymers which, when introduced into water at 25° C., at a weight concentration equal to 0.1%, produce a macroscopically homogeneous and transparent or translucent solution or suspension, i.e., a solution or suspension having a light transmittance value, at a wavelength equal to 500 nm, through a sample 1 cm thick, of at least 70% and preferably of at least 80%.

This ability to be dissolved or finely dispersed in water is linked to the high proportion of hydrophilic blocks in the amphiphilic block copolymers.

This proportion must be at least 30% by weight and is preferably greater than or equal to 60% by weight, without, however, exceeding 97% by weight.

The block polymers of the invention may be prepared by the synthetic processes conventionally used for obtaining block polymers. Examples that may be mentioned include anionic or cationic polymerization, and controlled free-radical polymerization (see "*New Method of Polymer Synthesis*", Blackie Academic & Professional, London, 1995, volume 2, page 1, or Trends Polym. Sci. 4, page 183 (1996) from C. J. Hawker), which may be used in various processes, for instance atom transfer radical polymerization (ATRP) (see *JACS*, 117, page 5614 (1995), from Matyjasezwski et al.), and the method with free radicals such as nitroxides (Georges et al., Macromolecules, 1993, 26, 2987).

These processes may also be used to obtain only one of the two types of blocks in the polymer of the invention, the other block being introduced into the final polymer by means of the initiator used, or alternatively via a coupling reaction between the hydrophilic and hydrophobic blocks.

The amount of amphiphilic linear block copolymers in the aqueous hair compositions of the present invention depends on a large number of parameters, among which mention may be made of the molecular mass of the copolymers, the number and size of the hydrophilic and hydrophobic blocks, the amount of polymers that are beneficial for the hair, and above all the viscosity of the composition that it is desired to obtain.

Satisfactory thickening or gelation is generally obtained with an amount of linear block copolymers of between 0.01 and 10% by weight and preferably between 0.1 and 5% by weight relative to the weight of the hair treatment composition.

The hair treatment compositions of the present invention contain at least one polymer that is beneficial for the hair.

This polymer may be of cationic, anionic, nonionic or amphoteric nature.

The cationic polymers are chosen, for example, from those described in patent applications EP 0 337 354, FR 2 270 846, FR 2 383 660, FR 2 598 611, FR 2 470 596 and FR 2 519 863.

The cationic polymers that are preferred are chosen from those containing units comprising primary, secondary, tertiary and/or quaternary amine groups which form part of the main macromolecular chain, or which are borne by side groups that are directly attached thereto.

Among the cationic polymers that may be mentioned more particularly are polymers of the polyamine, polyamino amide and polyquaternary ammonium type. These are known products.

The polymers of the polyamine, polyamino amide and polyquaternary ammonium type that may be used in accordance with the present invention, and that may especially be mentioned, are those described in French patents 2 505 348 or 2 542 997. Among these polymers, mention may be made in particular of:

(1) homopolymers or copolymers derived from acrylic or methacrylic esters or amides containing an amine function, comprising units of the following formulae:

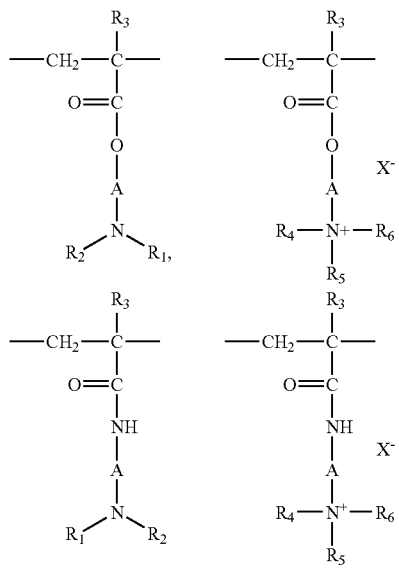

in which:

$R_3$, which may be identical or different, represent hydrogen or a $CH_3$ group;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl group and preferably an alkyl group containing from 1 to 6 carbon atoms;

$R_1$ and $R_2$, which may be identical or different, represent a hydrogen atom or an alkyl group containing from 1 to 6 carbon atoms, and preferably a methyl or ethyl group; and $X^{31}$ denotes an anion derived from a mineral or organic acid, such as a methosulphate anion or a halide such as chloride or bromide.

Copolymers of family (1) can also contain one or more units derived from comonomers which may be chosen from the family of acrylamides, methacrylamides, diacetone acrylamides, acrylamides and methacrylamides substituted on the nitrogen with $C_{1-4}$ lower alkyl groups, groups derived from acrylic or methacrylic acids or esters thereof, from vinyllactams such as vinylpyrrolidone or vinylcaprolactam, or from vinyl esters.

Among these copolymers of family (1) that may in particular be mentioned are:

(a) copolymers of acrylamide and of dimethylaminoethyl methacrylate quaternized with dimethyl sulphate or with a dimethyl halide, such as the product sold under the name Hercofloc by Hercules;

(b) the copolymers of acrylamide and of methacryloyloxyethyltrimethylammonium chloride described, for example, in patent application EP-A-080 976 and sold under the name Bina Quat P 100 by Ciba Geigy;

(c) the copolymer of acrylamide and of methacryloyloxyethyltrimethylammonium methosulphate sold under the name Reten by Hercules;

(d) quaternized or non-quaternized vinylpyrrolidone/dialkylaminoalkyl acrylate or methacrylate copolymers, such as the products sold under the name Gafquat® by ISP, such as, for example, Gafquat® 734 or Gafquat® 755, or alternatively the products known as Copolymer 845, 958 and 937. These polymers are described in detail in French patents 2 077 143 and 2 393 573;

(e) dimethylaminoethyl methacrylate/vinylcaprolactam/vinylpyrrolidone terpolymers, such as the product sold under the name Gaffix® VC 713 by ISP;

(f) vinylpyrrolidone/methacrylamidopropyldimethylamine copolymers sold especially under the name Styleze® CC 10 by ISP; and (g) quaternized vinylpyrrolidone/dimethylaminopropylmethacrylamide copolymers such as the product sold under the name Gafquat® HS 100 by ISP.

(2) The cellulose ether derivatives comprising quaternary ammonium groups, which are described in French patent 1 492 597, and in particular the polymers sold under the names "JR" (JR 400, JR 125, JR 30M) or "LR" (LR 400, LR 30M) by Union Carbide Corporation. These polymers are also defined in the CTFA dictionary as hydroxyethylcellulose quaternary ammoniums that have reacted with an epoxide substituted with a trimethylammonium group; and (3) Cationic cellulose derivatives such as the copolymers of cellulose or cellulose derivatives grafted with a water-soluble quaternary ammonium monomer, described especially in U.S. Pat. No. 4,131,576, such as hydroxyalkylcelluloses, for instance hydroxymethyl-, hydroxyethyl- or hydroxypropyl-celluloses grafted especially with a methacryloyl-ethyltrimethylammonium, methacrylamidopropyltrimethylammonium or dimethyldiallylammonium salt.

The commercial products corresponding to this definition are more particularly the products sold under the name Celquat® L 200 and Celquat® H 100 by National Starch;

(4) The cationic polysaccharides described more particularly in U.S. Pat. Nos. 3,589,578 and 4,031,307, such as guar gums containing trialkylammonium cationic groups. Use is made, for example, of guar gums modified with a salt (e.g. chloride) of 2,3-epoxypropyltrimethylammonium.

Such products are sold especially under the trade names Jaguar® C13S, Jaguar® C15, Jaguar® C17 and Jaguar® C162 by Meyhall;

(5) Polymers consisting of piperazinyl units and of divalent alkylene or hydroxyalkylene radicals containing straight or branched chains, optionally interrupted with oxygen, sulphur or nitrogen atoms or with aromatic or heterocyclic rings, and also the oxidation and/or quaternization products of these polymers. Such polymers are described, in particular, in French patents 2 162 025 and 2 280 361;

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508;

(7) Polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl group contains from 1 to 4 carbon atoms and preferably denotes a methyl, ethyl or propyl group, and the alkylene group contains from 1 to 4 carbon atoms, and preferably denotes an ethylene group. Such polymers are described in particular in French patent 1 583 363.

Among these derivatives, mention may be made more particularly of the adipic acid/dimethylaminohydroxypropyl/diethylenetriamine polymers sold under the name Cartaretine® F, F4 or F8 by the company Sandoz;

(8) Polymers obtained by reaction of a polyalkylene polyamine containing two primary amine groups and at least one secondary amine group with a dicarboxylic acid chosen from diglycolic acid and saturated aliphatic dicarboxylic acids containing from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name Hercosett® 57 by Hercules Inc. or under the name PD 170 or Delsette® 101 by Hercules in the case of the adipic acid/epoxypropyl/diethylenetriamine copolymer;

(9) Cyclopolymers of alkyldiallylamine or of dialkyldiallylammonium, such as the homopolymers or copolymers containing, as main constituent of the chain, units corresponding to formula (Va) or (Vb):

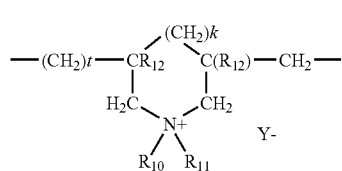

(Va)

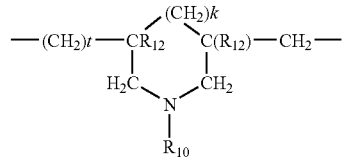

(Vb)

in which
k and t are equal to 0 or 1, the sum k+t being equal to 1;
$R_{12}$ denotes a hydrogen atom or a methyl radical;
$R_{10}$ and $R_{11}$, independently of each other, denote an alkyl group containing from 1 to 6 carbon atoms, a $C_{1-5}$ hydroxyalkyl group, a lower ($C_1$-$C_4$) amidoalkyl group, or $R_{10}$ and $R_{11}$ can denote, together with the nitrogen atom to which they are attached, heterocyclic groups such as piperidyl or morpholinyl;
$Y^{31}$ is an anion such as bromide, chloride, acetate, borate, citrate, tartrate, bisulphate, bisulphite, sulphate or phosphate.

These polymers are described in particular in French patent 2 080 759 and in its Certificate of Addition 2 190 406.

Among the polymers defined above; mention may be made more particularly of the dimethyldiallylammonium chloride homopolymer sold under the name Merquat® 100 by Calgon (and its homologues of low weight-average molecular mass) and copolymers of diallyldimethylammonium chloride and of acrylamide, sold under the name Merquat® 550;

(10) The quaternary diammonium polymers containing repeating units corresponding to formula (VI):

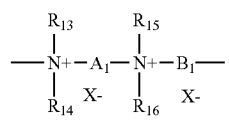

(VI)

in which:
$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second hetero atom other than nitrogen, or alternatively $R_{13}$, $R_{14}$, $R_{15}$ and $R_{16}$ represent a linear or branched $C_{1-6}$ alkyl radical substituted with a nitrile, ester, acyl or amide group or a group —CO—O—$R_{17}$-D or —CO—NH—$R_{17}$-D where $R_{17}$ is an alkylene group and D is a quaternary ammonium group;

$A_1$ and $B_1$ represent polymethylene groups containing from 2 to 20 carbon atoms, which groups may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups; and $X^{31}$ denotes an anion derived from a mineral or organic acid; and $A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group:

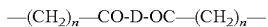

in which D denotes:

(a) a glycol residue of formula: —O—Z—O—, where Z denotes a linear or branched hydrocarbon-based radical or a group corresponding to one of the following formulae:

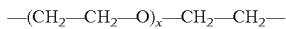

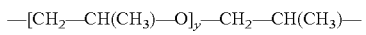

where x and y denote an integer from 1 to 4, representing a defined and unique degree of polymerization or any number from 1 to 4 representing an average degree of polymerization;

(b) a bis-secondary diamine residue such as a piperazine derivative;

(c) a bis-primary diamine residue of formula: —NH—Y—NH—, where Y denotes a linear or branched hydrocarbon-based radical, or alternatively the divalent radical —$CH_2$—$CH_2$—S—S—$CH_2$—$CH_2$—; and (d) a ureylene group of formula: —NH—CO—NH—.

Preferably, $X^{31}$ is an anion such as chloride or bromide.

These polymers generally have a number-average molecular mass of between 1000 and 100,000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the formula:

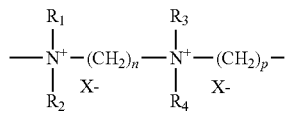

(VII)

in which $R_1$, $R_2$, $R_3$ and $R_4$, which may be identical or different, denote an alkyl or hydroxyalkyl group containing from 1 to 4 carbon atoms approximately, n and p are integers ranging from 2 to 20 approximately, and $X^{31}$ is an anion derived from a mineral or organic acid.

One compound of formula (VII) that is particularly preferred is the one for which $R_1$, $R_2$, $R_3$ and $R_4$ represent a methyl group and n=3, p=6 and X=Cl, which is known as Hexadimethrine chloride (CTFA);

(11) Polyquaternary ammonium polymers consisting of units of formula (VIII):

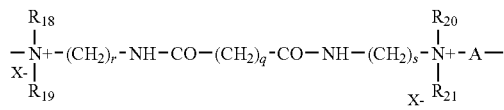

(VIII)

in which:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2(OCH_2CH_2)_p$OH radical, where p is equal to 0 or to an integer between 1 and 6, with the proviso that $R_{18}$, $R_{19}$, $R_{20}$ and $R_{21}$ do not simultaneously represent a hydrogen atom;

r and s, which may be identical or different, are integers ranging from 1 to 6;

q is equal to 0 or to an integer ranging from 1 to 34;

$X^{31}$ denotes an anion such as a halide; and

A denotes a dihalide radical or preferably represents —$CH_2$—$CH_2$—O—$CH_2$—$CH_2$—.

Such compounds are described in particular in patent application EP-A-122 324.

Among these products, mention may be made, for example, of "Mirapol® A 15", "Mirapol® AD1", "Mirapol® AZ1" and "Mirapol® 175" sold by Miranol;

(12) Quaternary polymers of vinylpyrrolidone and of vinylimidazole, such as, for example, the products sold under the names Luviquat® FC 905, FC 550 and FC 370 by BASF. Mention may be made especially of copolymers of vinylpyrrolidone and of methylvinylimidazolium chloride.

(13) Polyamines such as the product Polyquart® H sold by Cognis under the reference name "Polyethylene Glycol (15) Tallow Polyamine" in the CTFA dictionary; and

(14) Crosslinked or non-crosslinked methacryloyloxy ($C_{1-4}$)alkyltri-($C_{1-4}$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. An acrylamide/methacryloyloxyethyl-trimethylammonium chloride crosslinked copolymer (20/80 by weight) in the form of a dispersion containing 50% by weight of the said copolymer in mineral oil may be used more particularly. This dispersion is sold under the name Salcare® SC 92 by Allied Colloids. A crosslinked homopolymer of methacryloyloxyethyl trimethylammonium chloride containing about 50% by weight of the homo polymer in mineral oil or in a liquid ester may also be used. These dispersions are sold under the names Salcare® SC 95 and Salcare® SC 96 by Allied Colloids.

Other cationic polymers which can be used in the context of the invention are cationic proteins or cationic protein hydrolysates, polyalkyleneimines, in particular polyethyleneimines, polymers containing vinylpyridine or vinylpyridinium units, condensates of polyamines and of epichlorohydrin, quaternary polyureylenes, cationic chitin derivatives, and amino-functional silicones.

Among all the cationic polymers that may be used in the cosmetic compositions of the present invention, it is preferred to use cellulose ether derivatives comprising quaternary ammonium groups, such as the products sold under the name JR 400 by Union Carbide Corporation, cationic cyclopolymers, in particular the dimethyldiallylammonium chloride homopolymers or copolymers sold under the names Merquat® 100, Merquat® 550 and Merquat® S by the company Calgon, cationic polysaccharides such as guar gums modified with a 2,3-epoxypropyl trimethylammonium salt, quaternized copolymers of vinylpyrrolidone and of vinylimidazole, polyquaternary ammonium polycondensates preferably comprising the repeating units of formulae (VI) and (VIII) as indicated above, and mixtures thereof.

The beneficial anionic polymers generally used are polymers comprising groups derived from carboxylic acid, from sulphonic acid or from phosphoric acid and have a number-average molecular mass between about 500 and 5,000,000.

The carboxylic groups are provided by unsaturated monocarboxylic or dicarboxylic acid monomers such as those corresponding to the formula:

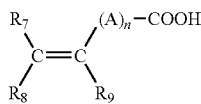

in which n is an integer from 0 to 10;

$A_1$ denotes a methylene group, optionally linked to the carbon atom of the unsaturated group or to the neighbouring methylene group when n is greater than 1, via a hetero atom such as oxygen or sulphur;

$R_7$ denotes a hydrogen atom or a phenyl or benzyl group;

$R_8$ denotes a hydrogen atom or a lower alkyl or carboxyl group; and $R_9$ denotes a hydrogen atom, a lower alkyl group or a —$CH_2$—COOH, phenyl or benzyl group.

In the abovementioned formula, a lower alkyl group preferably denotes a group containing 1 to 4 carbon atoms, and in particular methyl and ethyl groups.

The beneficial anionic polymers containing carboxylic groups that are preferred according to the invention are:

(A) Acrylic or methacrylic acid homo- or copolymers, or salts thereof and in particular the products sold under the names Versicol® E or K by Allied Colloid and Ultrahold by the company BASF, the copolymers of acrylic acid and of acrylamide sold in the form of their sodium salt under the names Reten® 421, 423 or 425 by Hercules and the sodium salts of polyhydroxycarboxylic acids;

(B) Copolymers of acrylic or methacrylic acid with a monoethylenic monomer such as ethylene, styrene, vinyl esters, acrylic or methacrylic acid esters, optionally grafted onto a polyalkylene glycol such as polyethylene glycol and optionally crosslinked. Such polymers are described in particular in French patent 1,222,944 and German patent application 2,330,956, the copolymers of this type containing an optionally N-alkylated and/or N-hydroxyalkylated acrylamide unit in their chain as described in particular in Luxembourg patent applications 75370 and 75371 or sold under the name Quadramer® by American Cyanamid. Mention may also be made of copolymers of acrylic acid and of $C_1$-$C_4$ alkyl methacrylate and terpolymers of vinylpyrrolidone, of acrylic acid and of methacrylate of $C_1$-$C_{20}$ alkyl, for example lauryl such as the product sold by ISP under the name Acrylidone® LM and methacrylic acid/ethyl acrylate/tert-butyl acrylate terpolymers such as the product sold under the name Luvimer® 100 P by BASF;

(C) Copolymers derived from crotonic acid such as those containing vinyl acetate or propionate units in their chain and optionally other monomers such as allylic esters or methallylic esters, vinyl ether or vinyl ester of a linear or branched saturated carboxylic acid with a long hydrocarbon chain such as those containing at least 5 carbon atoms, it being possible for these polymers optionally to be grafted and crosslinked, or alternatively a vinyl, allylic or methallylic ester of an α- or β-cyclic carboxylic acid. Such polymers are described, inter alia, in French patents 1 222 944, 1 580 545, 2 265 782, 2 265 781, 1 564 110 and 2 439 798. Commercial products falling into this class are the resins 28-29-30, 26-13-14 and 28-13-10 sold by National Starch;

(D) Copolymers derived from $C_4$-$C_8$ monounsaturated carboxylic acids or anhydrides chosen from:

(1) copolymers comprising (i) one or more maleic, fumaric or itaconic acids or anhydrides and (ii) at least one monomer chosen from vinyl esters, vinyl ethers, vinyl halides, phenylvinyl derivatives, acrylic acid and esters thereof, the anhydride functions of these copolymers optionally being monoesterified or monoamidated. Such polymers are described in particular in U.S. Pat. Nos. 2,047,398, 2,723,248 and 2,102,113 and GB patent 839 805 and in particular those sold under the names Gantrez® AN or ES by ISP; and (2) copolymers comprising (i) one or more maleic, citraconic or itaconic anhydride units and (ii) one or more monomers chosen from allylic or methallylic esters optionally containing one or more acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated;

These polymers are described, for example, in French patents 2 350 384 and 2 357 241 by the assignee.

(E) Polyacrylamides containing carboxylate groups;

The polymers comprising sulphonic groups are polymers containing vinylsulphonic, styrenesulphonic, naphthalenesulphonic or acrylamido alkylsulphonic units.

These polymers can be chosen in particular from:

(1) polyvinylsulphonic acid salts having a molecular mass of approximately between 1000 and 100,000, as well as the copolymers with an unsaturated comonomer such as acrylic or methacrylic acids and their esters, as well as acrylamide or its derivatives, vinyl ethers and vinylpyrrolidone;

(2) polystyrenesulphonic acid salts such as the sodium salts which are sold for example under the names Flexan® 500 and Flexan® 130 by National Starch. These compounds are described in French patent 2 198 719; and (3) polyacrylamidesulphonic acid salts, those mentioned in U.S. Pat. No. 4,128,631 and more particularly polyacrylamidoethylpropanesulphonic acid sold under the name Cosmedia Polymer® HSP 1180 by Henkel.

The beneficial amphoteric polymers that may be used in the hair compositions of the present invention may be chosen from polymers comprising units B and C randomly distributed in the polymer chain, in which B denotes a unit derived from a monomer comprising at least one basic nitrogen atom and C denotes a unit derived from a monomer comprising one or more carboxylic or sulphonic groups. The beneficial amphoteric polymers may also comprise zwitterionic units of carboxybetain or sulphobetain type.

They may also be polymers containing a cationic main chain comprising primary, secondary, tertiary or quaternary amine groups, among which at least one bears, via a hydrocarbon-based radical, a carboxylic acid or sulphonic acid group. The beneficial amphoteric polymers may also have an anionic chain derived from α,β-unsaturated carboxylic acids, one of the carboxyl groups of which has been reacted with a polyamine comprising one or more primary amine groups.

The beneficial amphoteric polymers corresponding to the definition given above are chosen especially from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides. Such compounds are described in U.S. Pat. No. 3,836,537;

(2) polymers containing units derived from:

(a) at least one monomer chosen from acrylamides and methacrylamides substituted on the nitrogen atom with an alkyl radical;

(b) at least one acidic comonomer containing one or more reactive carboxylic groups; and (c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer® or Lovocryl® 47 by National Starch are particularly used;

(3) crosslinked and partially or totally alkylated polyamino amides derived from polyamino amides of general formula:

—(CO—$R_{10}$—CO—Z—)—3 in which $R_{10}$ represents a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of the said acids to a bis(primary) or bis(secondary) amine, and Z denotes a bis (primary), mono- or bis(secondary) polyalkylene-polyamine radical and preferably represents:

(a) in proportions of from 60 to 100 mol %, the

—NH—[(CH$_2$)$_x$—NH]$_p$— group, where x=2 and p=2 or 3, or alternatively x=3 and p=2 this radical being derived from diethylenetriamine, from triethylenetetraamine or from dipropylenetriamine;

(b) in proportions of from 0 to 40 mol %, the

—NH—[(CH$_2$)$_x$—NH]$_p$— group in which x=2 and p=1 and which is derived from ethylenediamine, or the group derived from piperazine:

—N⌒N—

(c) in proportions of from 0 to 20 mol %, the

—NH—(CH$_2$)$_6$—NH— group derived from hexamethylenediamine, these polyaminoamides being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the alkylation are preferably propane sultone or butane sultone, the salts of the alkylating agents are preferably the sodium or potassium salts;

(4) polymers containing zwitterionic units of formula:

$$R_{11} \begin{bmatrix} R_{12} \\ | \\ C \\ | \\ R_{13} \end{bmatrix}_y \begin{matrix} R_{14} \\ | \\ N^+ \\ | \\ R_{15} \end{matrix} (CH_2)_Z - C - O^-$$

in which $R_{11}$ denotes a polymerizable unsaturated group such as an acrylate, methacrylate, acrylamide or methacrylamide group, y and z each represent an integer from 1 to 3, $R_{12}$ and $R_{13}$ represent a hydrogen atom, a methyl, ethyl or propyl group, $R_{14}$ and $R_{15}$ represent a hydrogen atom or an alkyl radical such that the sum of the carbon atoms in $R_{14}$ and $R_{15}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of methyl methacrylate/dimethyl carboxymethylammonio methyl ethylmethacrylate such as the product sold under the name Diaformer® Z301 by Sandoz;

(5) polymers derived from chitosan comprising monomer units corresponding to the following formulae:

(A)

[chemical structure of N-acetylglucosamine unit with CH$_2$OH, OH, H, NHCOCH$_3$ substituents]

(B)

[chemical structure of glucosamine unit with CH$_2$OH, OH, H, NH$_2$ substituents]

-continued

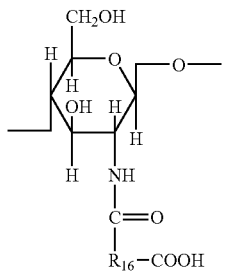
(C)

the unit (A) being present in proportions of between 0 and 30%, the unit (B) in proportions of between 5 and 50% and the unit (C) in proportions of between 30 and 90%, it being understood that, in this unit (C), $R_{16}$ represents a group of formula:

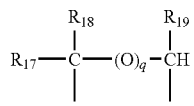

in which if q=0, $R_{17}$, $R_{18}$ and $R_{19}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulphonic groups, an alkylthio residue in which the alkyl group bears an amino residue, at least one of the radicals $R_{17}$, $R_{18}$ and $R_{19}$ being, in this case, a hydrogen atom;

or, if q=1, $R_{17}$, $R_{18}$ and $R_{19}$ each represent a hydrogen atom, as well as the salts formed by these compounds with bases or acids;

(6) Polymers derived from the N-carboxylation of chitosan, such as N-carboxymethylchitosan or N-carboxybutylchitosan sold under the name Evalsan® by Jan Dekker;

(7) The polymers described in French patent 1 400 366 and corresponding to the formula:

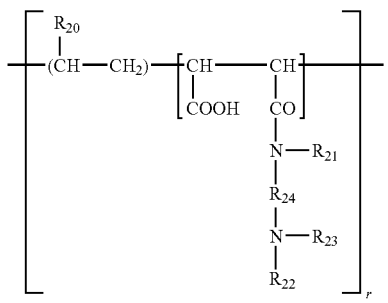

in which $R_{20}$ represents a hydrogen atom, a $CH_3O$, $CH_3CH_2O$ or phenyl radical, $R_{21}$ denotes a hydrogen atom or a lower alkyl group such as methyl or ethyl, $R_{22}$ denotes a hydrogen atom or a $C_1$-$C_6$ lower alkyl group such as methyl or ethyl, $R_{23}$ denotes a $C_1$-$C_6$ lower alkyl group such as methyl or ethyl or a group corresponding to the formula: $—R_{24}—N(R_{22})_2$, $R_{24}$ representing a $—CH_2—CH_2—$, $—CH_2—CH_2—CH_2—$ or $—CH_2—CH(CH_3)—$ group, $R_{22}$ having the meanings mentioned above;

(8) Amphoteric polymers of the type —D—X—D—X chosen from:

(a) polymers obtained by the action of chloroacetic acid or sodium chloroacetate on compounds containing at least one unit of formula:

—D—X—D—X—D— where D denotes a group

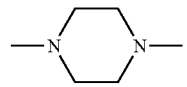

and X denotes the symbol E or E', E or E', which may be identical or different, denote a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups; and (b) polymers of formula:

-D-X-D-X— in which D denotes a group

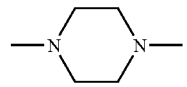

and X denotes the symbol E or E' and at least once E'; E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate;

(9) ($C_1$-$C_5$)alkyl vinyl ether/maleic anhydride copolymers, the maleic anhydride being partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The beneficial nonionic polymers are chosen, for example, from:

(a) polyvinylpyrrolidone;

(b) copolymers of vinylpyrrolidone and vinyl acetate;

(c) polyalkyloxazolines such as the polyethyloxazolines sold by the company Dow Chemical under the names Peox® 50 000, Peox® 200 000 and Peox® 500 000, (d) vinyl acetate homopolymers, such as the product sold under the name Appretan® EM by Hoechst, or the product sold under the name Rhodopas® A 012 by Rhône-Poulenc;

(e) copolymers of vinyl acetate and acrylic ester, such as the product sold under the name Rhodopas® AD 310 by Rhône-Poulenc;

(f) copolymers of vinyl acetate and ethylene, such as the product sold under the name Appretan® TV by the company Hoechst;

(g) copolymers of vinyl acetate and maleic ester, for example of dibutyl maleate, such as the product sold under the name Appretane® MB Extra by the company Hoechst, (h) copolymers of polyethylene and maleic anhydride;

(i) poly(alkyl acrylates) and poly(alkyl methacrylates) such as the product sold under the name Micropearl® RQ 750 by the company Matsumoto or the product sold under the name Luhydran® A 848 S by BASF; or alkyl acrylate homopolymers and alkyl methacrylate homopolymers, (j) acrylic ester copolymers such as, for example, copolymers of alkyl acrylates and alkyl methacrylates, such as the products sold by the company Rohm & Haas under the names Primal® AC-261 K and Eudragit® NE 30 D, by the company BASF under the names Acronal® 601, Luhydran® LR 8833 or 8845, and by the company Hoechst under the names Appretan® N 9212 or N 9213, (k) copolymers of acrylonitrile and a nonionic monomer chosen, for example, from butadiene and alkyl (meth)acrylates; mention may be made of the products sold under the names Nipol® LX 531 B by the company Nippon Zeon or those sold under the name CJ 0601 B by the company Rohm & Haas, (l) polyamides, such as the product Estapor® LO 11 sold by the company Rhône-Poulenc, (m) unmodified or chemically modified nonionic guar gums. The unmodified guar gums are, for example, the products sold under the name Vidogum® GH 175 by the company Unipectine and under the name Jaguar® C by the company Meyhall. The modified guar gums are preferably modified with $C_1$-$C_6$ hydroxyalkyl groups, and preferably hydroxymethyl, hydroxyethyl, hydroxypropyl and hydroxybutyl groups. Such nonionic guar gums optionally modified with hydroxyalkyl groups are sold, for example, under the trade names Jaguar® HP8, Jaguar® HP60 and Jaguar® HP 120, Jaguar® DC 293 and Jaguar® HP 105 by the company Meyhall or under the name Galactasol® 4H4FD2 by the company Aqualon.

(n) copolymers of vinylpyrrolidone and of vimylcapro;actam.

It is also possible to use as beneficial polymers film-forming polymers of grafted silicone type comprising a polysiloxane portion and a portion consisting of a non-silicone organic chain, one of the two portions constituting the main chain of the polymer and the other being grafted onto the said main chain.

These polymers are described, for example, in patent applications EP-A-0 412 704, EP-A-0 412 707, EP-A-0 640 105 and WO 95/00578, EP-A-0582 152 and WO 93/23009 and U.S. Pat. Nos. 4,693,935, 4,728,571 and 4,972,037.

These polymers may be anionic, cationic, nonionic or amphoteric, but are preferably anionic or nonionic.

Such polymers are, for example, copolymers capable of being obtained by free-radical polymerization from a monomer mixture formed from:

(a) 50% to 90% by weight of tert-butyl acrylate;

(b) 0% to 40% by weight of acrylic acid; and (c) 5% to 40% by weight of a silicone macromer of formula:

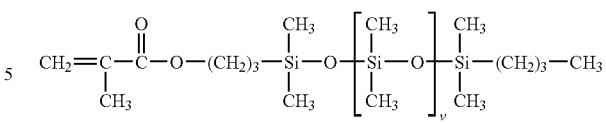

in which v is a number ranging from 5 to 700, the weight percentages being calculated relative to the total weight of the monomers.

Other examples of grafted silicone polymers are especially polydimethylsiloxanes (PDMS) on which are grafted, via a connecting chain unit of thiopropylene type, mixed polymer units of the poly(meth)acrylic acid type and of the polyalkyl (meth)acrylate type, and polydimethylsiloxanes (PDMS) on which are grafted, via a connecting chain unit of thiopropylene type, polymer units of the polyisobutyl (meth)acrylate type.

Polymers containing urethane units may also be used. These polyurethanes may be functionalized or unfunctionalized, silicone or non-silicone, and cationic, nonionic, anionic or amphoteric. The polyurethanes that are particularly targeted are those described in patent applications EP 0 751 162, EP 0 637 600, EP 0 648 485 and FR 2 743 297, of which the assignee is the proprietor, and also in patent applications EP 0 656 021 and WO 94/03510 from BASF, and in patent application EP 0 619 111 from National Starch. As polyurethanes that are particularly suitable for the present invention, mention may be made of the products sold under the names Luviset Pur® and Luviset® Si Pur by BASF.

The beneficial polymers, i.e. the fixing and/or conditioning polymers, are present in the hair treatment compositions of the present invention in an amount that is sufficient to obtain the cosmetic effect obtained.

This amount is generally between 0.01% and 20% by weight and preferably between 0.1 and 10% by weight.

The cosmetically acceptable aqueous medium may consist solely of water or of a mixture of water and one or more cosmetically acceptable water-miscible solvents such as $C_1$-$C_4$ lower alcohols, in particular ethanol, isopropanol, tert-butanol and n-butanol.

The compositions according to the invention may also contain cosmetic additives and/or formulation adjuvants such as volatile or non-volatile silicones, anionic, cationic, amphoteric or nonionic surfactants, nacreous agents, opacifiers, pigments and dyes, oils, waxes, including ceramides, organic or mineral UV-screening agents, free-radical scavengers, vitamins, proteins, antidandruff agents, plasticizers, pH adjusting and fixing agents, antioxidants, preserving agents, hair dye precursors and oxidizing agents.

A person skilled in the art will take care to select the optional additives and the amount thereof such that they do not harm the advantageous properties of the compositions of the present invention.

The hair treatment compositions of the present invention, which are thickened or gelled by using linear block copolymers as described above, may be in any form that allows easy application to the hair. They preferably are thickened lotions, aqueous or aqueous-alcoholic gels, creams or pastes that are more or less hard.

These compositions may be packaged in an aerosol device in the presence of one or more propellants. These propellants are preferably chosen from dimethyl ether, $C_{3-5}$ alkanes, 1,1-difluoroethane, mixtures of dimethyl ether and of $C_{3-5}$ alkanes and mixtures of 1,1-difluoroethane and of dimethyl ether and/or of $C_{3-5}$ alkanes The present invention is illustrated below with the aid of an example.

EXAMPLE

The styling gels below are prepared, containing, as fixing polymer, 2% by weight of polyvinylpyrrolidone (PVP), respectively gelled with a polymer according to the prior art (comparative example), a diblock block copolymer according to the invention (Composition A) and a triblock block copolymer according to the invention (Composition B).

|  | Comparative example | Composition A | Composition B |
|---|---|---|---|
| Crosslinked poly(acrylic acid)[a] | 1% | | |
| Diblock block copolymer[b] | | 1% | |
| Triblock block copolymer[c] | | | 1% |
| Polyvinylpyrrolidone[d] (fixing polymer) | 2% | 2% | 2% |
| Fragrance | qs | qs | qs |
| Ethanol | 10% | 10% | 10% |
| Aminomethylpropanol | qs pH 7 | qs pH 7 | qs pH 7 |
| Water | qs. 100% | qs. 100% | qs. 100% |

[a]SYNTHALEN ® K sold by 3V
[b]poly(styrene-b-acrylic acid), sold by Polymer Source Inc.:
molecular mass of the styrene block: 1 500
molecular mass of the acrylic acid block: 44 000
[c]poly(styrene-b-acrylic acid-b-styrene), sold by Polymer Source Inc.
molecular mass of each styrene block: 1 000
molecular mass of the acrylic acid block: 40 000
[d]PVP K30 sold by ISP Each of the compositions A and B and also the composition of the comparative example are applied to 10 heads of short (5 to 10 cm) chestnut-brown European hair, at a rate of 5 g per head of hair.

The hold properties of hair treated with the three compositions above are evaluated by 5 experts according to a grading scale ranging from 0 (absence of fixing) to 5 (very high fixing). The figures indicated below correspond to the average of the grades given by all the experts.

| Composition A (according to the invention): | 4.3 |
|---|---|
| Composition B (according to the invention): | 4.7 |
| Comparative example: | 3.4 |

These results show that the amphiphilic linear block copolymers used in accordance with the invention to thicken styling compositions reinforce the desired effect, i.e. the fixing effect. Specifically, the level of fixing obtained with the compositions according to the present invention (fixing polymer+diblock or triblock amphiphilic block copolymer) is significantly higher than that obtained with a composition of the prior art (fixing polymer+thickening polymer of Carbopol type).

The use of amphiphilic linear block copolymers in styling compositions thus makes it possible to obtain a higher level of fixing without increasing the concentration of fixing polymer. This is always an advantage when the fixing polymer gives rise, above a certain amount, to undesirable effects such as a dull appearance or a powdering effect.

We claim:

1. A hair treatment composition comprising, in an aqueous cosmetically acceptable medium:
    (a) at least one non-ionic fixing polymer that has a beneficial effect on the hair chosen from polyvinylpyrrolidone, a copolymer of vinylpyrrolidone and vinylcaprolactam, a vinyl acetate homopolymer, a polyalkyloxazoline, a copolymer of vinyl acetate and alkyl maleate, an alkyl acrylate homopolymer, an alkyl methacrylate homopolymer, a copolymer of acrylic and methacrylic ester, a copolymer of acrylonitrile and a nonionic comonomer, a polyamide, a nonionic polyurethane or a nonionic silicone polymer; and
    (b) at least one water-soluble or water-dispersible linear diblock or triblock copolymer, the blocks being homopolymer blocks, comprising
        at least one hydrophilic block, chosen from ethylenically unsaturated carboxylic acid, 2-acrylamido-2-methylpropanesulphonic acid, a styrene-sulphonic acid, a vinylsulphonic acid or a vinylphosphonic acid and
        at least one hydrophobic block chosen from vinylaromatic monomer, a diene or alkyl derivative of a diene, chloroprene, a $C_{1-10}$ alkyl, $C_{6-10}$ aryl or $C_{6-10}$ aralkyl acrylate, a $C_{1-10}$ alkyl, $C_{6-10}$ aryl or $C_{1-10}$ aralkyl methacrylate, vinyl acetate, vinylether of formula $CH_2=CH-O-R$ or allylether of formula $CH_2=CH-CH_2-O-R$ in which R represents a $C_{1-6}$ alkyl group, acrylonitrile, vinyl chloride, vinylidene chloride, caprolactone, ethylene, propylene or vinyl monomer that is fluorinated or that contains a perfluoro chain
        the hydrophilic block representing at least 30% by weight of the linear block copolymer, with the exclusion of block copolymers of ethylene oxide and propylene oxide, block copolymers containing urethane units and block copolymers containing siloxane units,
        in an amount that is sufficient to thicken or gel the composition, the copolymer being present in a proportion of from 0.01% to 10% by weight relative to the hair composition.

2. The hair treatment composition according to claim 1, wherein the hydrophilic block represents at least 60% by weight of the linear block copolymer.

3. The hair treatment composition according to claim 1, wherein the at least water-soluble or water-dispersible linear diblock copolymer or triblock copolymer comprises a hydrophilic central block and two hydrophobic side blocks.

4. The hair treatment composition according to claim 1, wherein the hydrophilic block contains up to 25 mol % of one or more water-insoluble monomers.

5. The hair treatment composition according to claim 4, wherein the hydrophilic block contains up to 10 mol % of one or more water-insoluble monomers.

6. The hair treatment composition according to claim 4, wherein the hydrophilic block contains up to 5 mol % of one or more water-insoluble monomers.

7. The hair treatment composition according to claim 1, wherein the hydrophobic block contains up to 25 mol % of one or more water-soluble monomers.

8. The hair treatment composition according to claim 7, wherein the hydrophobic block contains up to 10 mol % of one or more water-soluble monomers.

9. The hair treatment composition according to claim 7, wherein the hydrophobic block contains up to 5 mol % of one or more water-soluble monomers.

10. The hair treatment composition according to claim 1, wherein the at least one water-soluble or water-dispersible linear diblock or triblock copolymer is present in a proportion of from 0.1% to 5% by weight relative to the hair treatment composition.

11. The hair treatment composition according to claim 1, wherein the non-ionic fixing polymer that is beneficial for the hair is present in a proportion of from 0.0 1% to 20% by weight.

12. The hair treatment composition according to claim 11, wherein the non-ionic fixing polymer that is beneficial for the hair is present in a proportion of from 0.1% to 10% by weight.

13. The hair treatment composition according to claim 1, wherein the composition also comprises a cosmetic additive or formulation adjuvant which is a volatile or non-volatile silicone, an anionic, cationic, amphoteric or nonionic surfactant, a nacreous agent, an opacifier, a pigment or colorant, an oil, a wax, a ceramide, an organic or mineral UV-screening agent, a free-radical scavenger, a plasticizer, a vitamin, a protein, an antidandruff agent, an agent for adjusting or fixing the pH, an antioxidant, a preserving agent, a hair dye precursor or an oxidizing agent.

14. The hair treatment composition according to claim 1, wherein the composition is in the form of a thickened lotion, a gel, a cream or a paste.

15. A method of thickening or gelling an aqueous hair treatment composition containing at least one non-ionic fixing polymer chosen from copolymers of vinylpyrrolidone and of vinylcaprolactam, vinyl acetate homopolymers, polyalkyloxazolines, copolymers of vinyl acetate and of alkyl maleate, alkyl acrylate homopolymers, alkyl methacrylate homopolymers, copolymers of acrylic and methacrylic esters, copolymers of acrylonitrile and of nonionic comonomers, polyamides, nonionic polyurethanes and nonionic silicone polymers; and consisting essentially of adding to the composition, in an aqueous cosmetically acceptable medium, at least one water-soluble or water-dispersible linear diblock or triblock copolymer, the blocks being homopolymer blocks comprising at least one hydrophilic block chosen from ethylenically unsaturated carboxylic acid, 2-acrylamido-2-methyl-propanesulphonic acid, styrene-sulphonic acid, vinylsuiphonic acid and vinylphosphonic acid and at least one hydrophobic block chosen from vinylaromatic monomer, diene and alkyl derivative of diene, chioroprene, a $C_{1-10}$ alkyl, $C_{6-10}$ aryl or $C_{6-10}$ aralkyl acrylate, a $C_{1-10}$ alkyl, $C_{6-10}$ aryl or $C_{1-10}$ aralkyl methacrylate, vinyl acetate, vinylether of formula $CH_2=CH-O-R$ or allylether of formula $CH_2=CH-CH_2-O-R$ in which R represents a $C_{1-6}$ alkyl group, acrylonitrile, vinyl chloride, vinylidene chloride, caprolactone, ethylene, propylene or vinyl monomer that is fluorinated or that contains a perfluoro chain, the hydrophilic block representing at least 30% by weight of the linear block copolymer, with the exclusion of block copolymers of ethylene oxide and propylene oxide, block copolymers containing urethane units and block copolymers containing siloxane units, in an amount that is sufficient to thicken or gel the composition, the copolymer being present in a proportion of from 0.01% to 10% by weight relative to the hair composition.

* * * * *